United States Patent
Adkison

(10) Patent No.: US 12,193,682 B2
(45) Date of Patent: Jan. 14, 2025

(54) SURGICAL TOOL AND METHOD OF USE

(71) Applicant: Howmedica Osteonics Corp., Mahwah, NJ (US)

(72) Inventor: David P. Adkison, Mountain Brook, AL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 771 days.

(21) Appl. No.: 17/263,043

(22) PCT Filed: Jul. 25, 2019

(86) PCT No.: PCT/US2019/043392
§ 371 (c)(1),
(2) Date: Jan. 25, 2021

(87) PCT Pub. No.: WO2020/023722
PCT Pub. Date: Jan. 30, 2020

(65) Prior Publication Data
US 2021/0228217 A1    Jul. 29, 2021

Related U.S. Application Data

(60) Provisional application No. 62/776,077, filed on Dec. 6, 2018, provisional application No. 62/703,230, filed on Jul. 25, 2018.

(51) Int. Cl.
*A61B 17/15* (2006.01)
*A61B 17/16* (2006.01)
(Continued)

(52) U.S. Cl.
CPC .......... *A61B 17/15* (2013.01); *A61B 17/1778* (2016.11); *A61F 2/4612* (2013.01);
(Continued)

(58) Field of Classification Search
CPC ... A61B 17/15; A61B 17/1778; A61B 17/151; A61B 17/17; A61B 17/1714;
(Continued)

(56) References Cited

U.S. PATENT DOCUMENTS 5,222,955 A * 6/1993 Mikhail ............ A61B 17/1767
606/80
5,324,295 A    6/1994 Shapiro
(Continued)

FOREIGN PATENT DOCUMENTS

WO    2006136955 A1    12/2006
WO    2018045160 A1    3/2018

OTHER PUBLICATIONS

Extended European Search Report issued in Appln. No. 19841642.2 dated Feb. 16, 2022. (3 pages).
(Continued)

*Primary Examiner* — Marcela I. Shirsat
(74) *Attorney, Agent, or Firm* — Lerner David LLP

(57) ABSTRACT

The present disclosure generally relates to a surgical tool for use in shoulder arthroplasty. The surgical tool includes a humeral head cut guide configured to fit within a rotator interval of a subject in need of shoulder arthroplasty. The cut guide can further include a top surface, a bottom surface, a front surface, a back surface, and at least two sides. The surgical tool can also have at least two nonconverging pin holes and a receiving portion configured to permit reversible attachment of the cut guide to an attachment arm assembly.

26 Claims, 17 Drawing Sheets

(51) Int. Cl.
*A61B 17/17* (2006.01)
*A61F 2/40* (2006.01)
*A61F 2/46* (2006.01)

(52) U.S. Cl.
CPC ......... *A61B 17/151* (2013.01); *A61B 17/1642* (2013.01); *A61B 17/1657* (2013.01); *A61B 17/1684* (2013.01); *A61B 17/175* (2013.01); *A61B 17/1789* (2016.11); *A61F 2/4003* (2013.01); *A61F 2002/4011* (2013.01); *A61F 2/4014* (2013.01); *A61F 2002/4018* (2013.01); *A61F 2002/4022* (2013.01); *A61F 2/4081* (2013.01); *A61F 2002/4619* (2013.01)

(58) Field of Classification Search
CPC ............ A61B 17/1642; A61B 17/1657; A61B 17/1684; A61B 17/1662; A61B 17/1739; A61B 17/175; A61F 2/4612; A61F 2/46; A61F 2/40; A61F 2/4003; A61F 2/4014; A61F 2/581; A61F 2/4637; A61F 2/4081; A61F 2002/4619; A61F 2002/4011; A61F 2002/4018; A61F 2002/4022; A61F 2002/4658; A61F 2002/4668; A61F 2007/003
USPC .............. 606/87, 91, 86 R, 96–98, 103, 104; 623/16.11, 19.11–19.14
See application file for complete search history.

(56) References Cited

U.S. PATENT DOCUMENTS

| | | | |
|---|---|---|---|
| 6,120,510 A * | 9/2000 | Albrektsson | A61B 17/15 606/88 |
| 2005/0043805 A1 | 2/2005 | Chudik | |
| 2006/0004373 A1* | 1/2006 | Ondrla | A61B 17/15 606/87 |
| 2009/0222010 A1* | 9/2009 | Lafosse | A61B 17/1778 606/86 R |
| 2009/0270864 A1 | 10/2009 | Poncet | |
| 2013/0096564 A1* | 4/2013 | Winslow | A61B 17/15 606/96 |
| 2013/0261629 A1 | 10/2013 | Anthony et al. | |
| 2013/0261755 A1* | 10/2013 | Anthony | A61F 2/4684 623/19.14 |
| 2014/0066933 A1 | 3/2014 | Ek et al. | |
| 2015/0320430 A1 | 11/2015 | Kehres et al. | |
| 2019/0175298 A1* | 6/2019 | Muir | A61B 90/35 |

OTHER PUBLICATIONS

International Search Report for Application No. PCT/US2019/043392 dated Oct. 2, 2019.

* cited by examiner

SURGICAL TOOL AND METHOD OF USE

This application is a § 371 national stage entry of PCT/US2019/043392, filed on Jul. 25, 2019, which claims priority from U.S. Provisional Application No. 62/703,230 filed on Jul. 25, 2018 and U.S. Provisional Application No. 62/776,077 filed on Dec. 6, 2018, the entire contents of which are incorporated herein by reference.

All patents, patent applications, and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

The present invention generally relates to tools and methods for shoulder surgeries.

SUMMARY OF THE INVENTION

The present disclosure generally relates to tools and methods for shoulder surgeries. In embodiments, the disclosure provides for a humeral head cut guide and methods of using the same.

One aspect disclosed herein is a surgical tool for use in shoulder arthroplasty. In one embodiment, the surgical tool includes a humeral head cut guide configured to fit within a rotator interval of a subject in need of shoulder arthroplasty. The cut guide can further include a top surface, a bottom surface, a front surface, a back surface, and at least two sides. The surgical tool can also have at least two nonconverging pin holes and a receiving portion configured to permit reversible attachment of the cut guide to an attachment arm assembly. In one embodiment, the cut guide is substantially trapezoidal in shape.

The front surface of the cut guide can be configured to fit securely on the humeral head of the subject. In one embodiment, the front surface of the cut guide is curved around an arc that is substantially complementary to the shape of the subject's humeral head.

Each pinhole or pin channel can extends from one side of the cut guide to the front surface of the cut guide. The cut guide can also include at least two setting spikes that extend outwardly from the front surface of the cut guide and are configured to assist with the placement of the cut guide. In one embodiment, the setting spikes extend about 2 to 3 mm from the front surface of the cut guide.

The cut guide can be a free cut resection guide. In an alternative embodiment, the cut comprises a channel configured to receive a blade of a surgical saw. In such embodiments, the channel extends from the back surface of the cut guide to the front surface of the cut guide and is configured to guide the blade during humeral head osteotomy.

In embodiments, the front surface of the cut guide is longer than the back surface of the cut guide. For example, the length of the front surface can be about 120% the length of the back surface. For example, the length of the front surface can be about 125% the length of the back surface. The front surface can be about 25 mm long, and the back surface can be about 20 mm long. The front surface can be about 30 mm long, and the back surface can be about 25 mm long. In one embodiment, the height of the cut guide is about 7 mm. At least one of the sides of the cut guide can be about 17 mm long. In one embodiment, the height of the cut guide is about 8 mm. At least one of the sides of the cut guide can be about 20 mm long.

The surgical tool can further comprise an attachment arm assembly. The attachment arm assembly can comprise a vertical arm, a horizontal arm, a set screw, a cut guide retaining rod, an anchoring rod, or a combination thereof. The cut guide retaining rod can be configured to reversibly secure the cut guide to the attachment arm assembly. In one embodiment, the receiving portion of the cut guide terminates in a threaded opening, and the cut guide retaining rod comprises a threaded portion that is complementary to the threaded opening of the cut guide.

Another aspect disclosed herein includes a method for total shoulder arthroplasty, the method can comprise one or more of the steps disclosed in Example 1.

In embodiments, the method includes performing total shoulder arthroplasty using the any one or any combination of the surgical tools described above. The surgical method comprises humeral head osteotomy through the rotator interval. In an embodiment, the method includes opening of the rotator interval. Opening of the rotator interval can include creating a trap door of rotator interval tissue and preserving the trap door for closing upon completion of the shoulder arthroplasty. In one embodiment, creating the trap door of rotator interval tissues includes any one or more of the following steps: cauterizing tissue from about 5 mm posterior to a long head of a subject's biceps tendon, wherein the incision exits the subject's shoulder joint and pierces the subject's coracohumeral ligament; carrying the incision down to the subject's articular insertion of the subject's subscapularis; identifying the longhead of the biceps; releasing the long head of the biceps from the subject's supraglenoid tubercle; tenodesing the long head of the biceps at the subject's transverse ligament; removing the biceps tendon from the rotator interval tissue; incising the rotator interval tissue back to the subject's glenoid from the upper edge of the subscapularis to create a triangular "trap door" attached to the subject's supraspinatus.

The method can further include identifying a raphe between the subject's middle and anterior deltoid; splitting the deltoid between the subject's anterior and middle heads of the deltoid; and rotating the subject's shoulder to bring the rotator interval into the field of view.

Embodiments of the method include the step of marking the subject's articular margin to be used a reference when placing the cut guide; inserting an anchoring rod of the attachment arm assembly into the subject's intramedullary canal; aligning the cut guide with the marked articular margin; pinning the cut guide in place over the articular margin; and removing the attachment arm assembly. The method can further include placing a blade of a surgical saw against the cut guide; cutting the subject's humeral head; and removing the cut humeral head through the rotator interval.

In embodiments, the method comprises resecting the subject's labrum; releasing at least a portion of the subject's inferior capsule from the subject's glenoid; and placing an artificial glenoid component onto the glenoid.

The method also includes inserting an artificial humeral head stem into the subject's humerus and impacting a humeral head prosthesis onto the artificial humeral head stem.

In embodiments, an extractor/insertor is provided or obtained. The extractor/insertor can be configured to extract and insert the artificial humeral head stem reversibly attached thereto. In one embodiment, the extractor/insertor comprises a strike plate; a vertical rod; an engagement mechanism; and a trigger. The step of inserting the artificial humeral head stem can include striking the strike plate to impact the humeral head stem within the humerus and depressing the trigger to free the humeral head stem component from the extractor/insertor. In an alternative embodiment, the extractor/insertor comprises a strike plate; a vertical rod; a pin that extends at least partially through the vertical rod; and a locking pin trigger. In the alternative embodiment, the step of inserting the artificial humeral head stem can include striking the strike plate to impact the humeral head stem within the humerus and depressing the locking pin to trigger freeing the humeral head stem component from the extractor/insertor.

In certain embodiments, a low profile curved impactor is provided or obtained. The curved impactor can include a strike plate. In embodiments with a curved impactor, the step of impacting the humeral head prosthesis onto the artificial humeral head stem includes aligning the impactor over the humeral head prosthesis and striking the strike plate of the impactor to set the humeral head prosthesis within the artificial humeral head stem.

The method can further include closing the trap door and closing the deltoid split.

Other objects and advantages of this invention will become readily apparent from the ensuing description.

DETAILED DESCRIPTION OF THE INVENTION

Abbreviations and Definitions

Figure 1A:
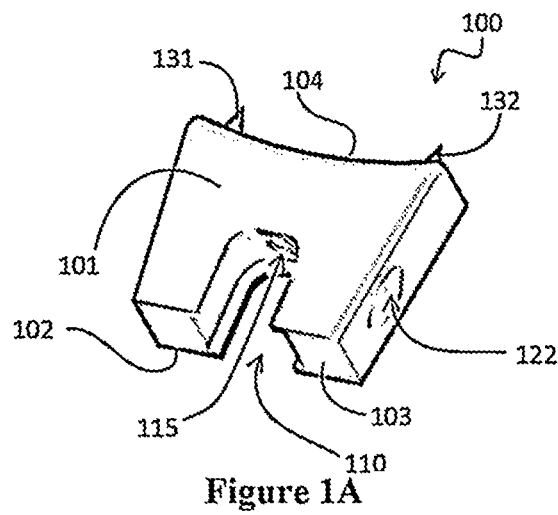
FIG. 1A shows a top perspective view of a humeral head cut guide under one embodiment.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a," "an," and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises," "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "about" can refer to approximately, roughly, around, or in the region of. When the term "about" is used in conjunction with a numerical range, it modifies that range by extending the boundaries above and below the numerical values set forth. In general, the term "about" can be used herein to modify a numerical value above and below the stated value by a variance of 20 percent up or down (higher or lower).

For purposes of the present disclosure, it is noted that spatially relative terms, such as "up," "down," "right," "left," "beneath," "below," "lower," "above," "upper" and the like, can be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device can be otherwise oriented (rotated 90 degrees or at other orientations) and the spatially relative descriptors used herein interpreted accordingly.

The terms "subject" and "patient" as used herein include all members of the animal kingdom including, but not limited to, mammals, animals (e.g., cats, dogs, horses, swine, etc.) and humans.

The terms "cutting guide," "cut guide," "cutting block," and "block" are used interchangeably to refer to the various exemplary embodiments of the humeral head cut guide.

The term "rotator interval" describes an anatomical space within the shoulder of a subject, the uppermost boundary of which is defined by the supraspinatus muscle tendon, and the lower boundary of which is defined by the subscapularis muscle tendons.

Description of Selected Embodiments

FIG. 1 provides various views of a humeral head cut guide 100 in one embodiment. The top surface 101 and the back surface 103 of the humeral head cut guide 100 are clearly seen in FIG. 1A. The guide 100 can include at least two setting spikes 131, 132 along the front surface 104 that are configured to assist with placement of the guide 100 during the rotator interval approach to shoulder arthroplasty (discussed in more detail below). In embodiments, the setting spikes 131, 132 extend about 0.5 to 5 mm from the front surface 104 of the cut guide 104. The setting spikes 131, 132, can extend about 1 to 4 mm from the front surface 104 of the cut guide 100. In one embodiment, the setting spikes 131, 132 extend about 2 to 3 mm from the front surface 104 of the cut guide 104.

Figure 1B:
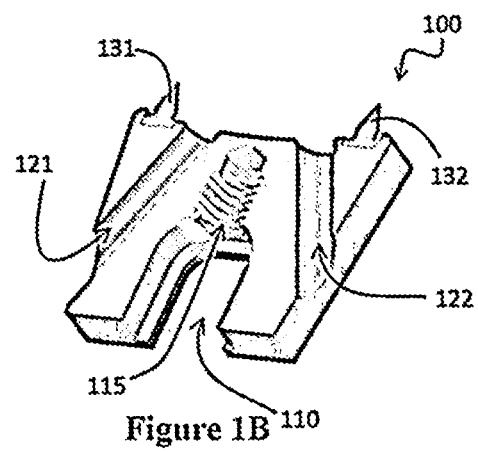
FIG. 1B shows a transverse cross-sectional top perspective view of the humeral head cut guide of FIG. 1A.

As clearly shown in the cross-sectional view of FIG. 1B, two non-converging pin holes or channels 121, 122 extend across the transverse axis of the guide 100. In operation, the pin holes 121, 122 receive surgical pins to secure the guide in place while the humeral head is cut. Each of the pin holes 121, 122 can comprise diameters that are substantially similar to the other. In embodiments, the pin holes 121, 122 have diameters that are distinct from one another. The diameter of at least one pin hole can be up to about 7 mm. In embodiments, the diameter of at least one pin hole can be between about 0.5 mm to about 7 mm, inclusive. The diameter of at least one pin hole can be between about 1 mm to about 5 mm. In certain embodiments, the diameter of at least one pin hole is about 1 mm, about 2 mm, about 3 mm, about 4 mm, about 5 mm, about 6 mm, about 7 mm, or about 8 mm. In one embodiment, the diameter of at least one pin hole is about 2.5 mm.

Figure 3A:
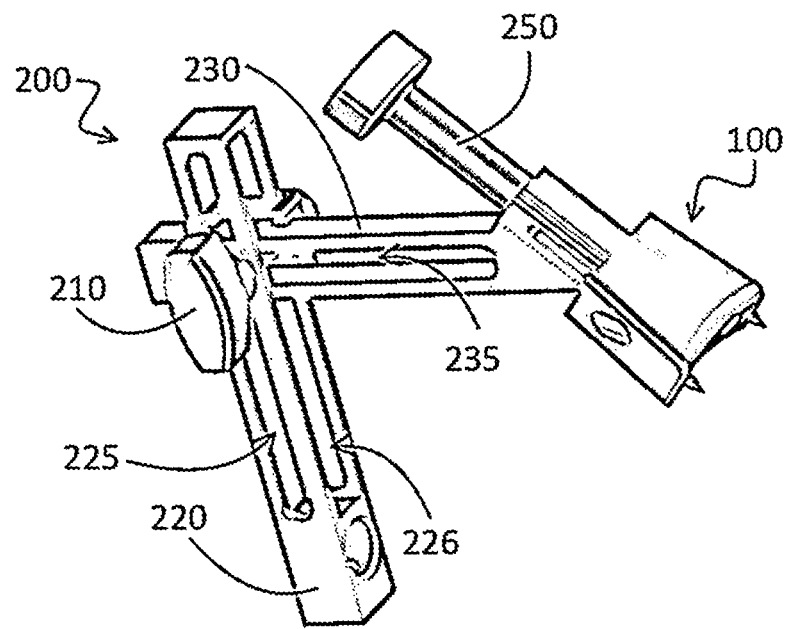
FIG. 3A shows a right side perspective view of an attachment arm assembly with the humeral head cut guide of FIG. 1 attached thereto.
Figure 3B:
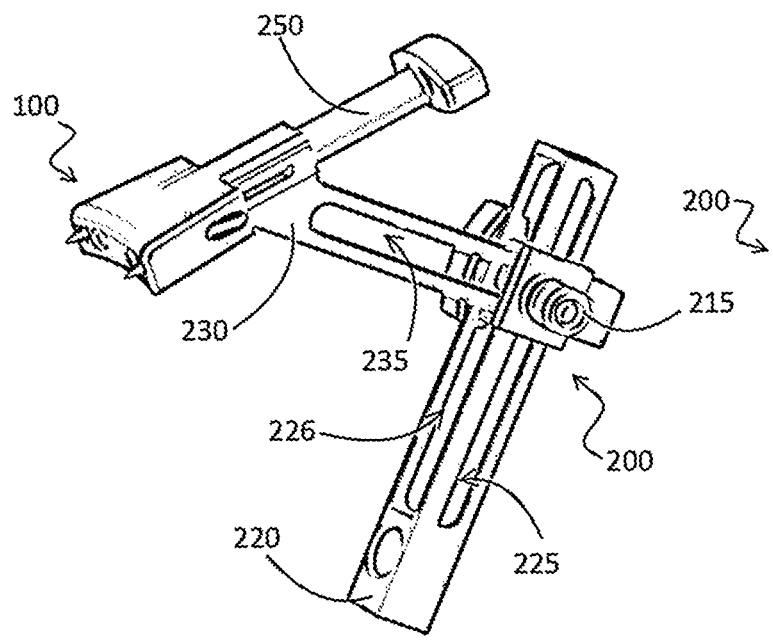
FIG. 3B shows a left side perspective view of an attachment arm assembly with the humeral head cut guide of FIG. 1 attached thereto.

The guide 100 includes a receiving portion 110 that is configured to permit reversible attachment of the guide 100 to an attachment arm assembly seen at 200 in FIGS. 3A-B. The receiving portion 100 terminates in a threaded opening 115 that extends partially into the guide 100 and is configured to further secure the guide 100 to the attachment arm assembly 200. In embodiments, the threaded portion of the threaded opening 115 is at least 0.2 mm long. The threaded portion can be between about 0.2 mm to about 0.7 mm long, inclusive. In embodiments, the threaded portion is about 0.2 mm, about 0.3 mm, about 0.4 mm, about 0.5 mm, about 0.6 mm, or about 0.7 mm long. In one embodiment, the threaded portion is about 0.5 mm long.

Figure 1C:
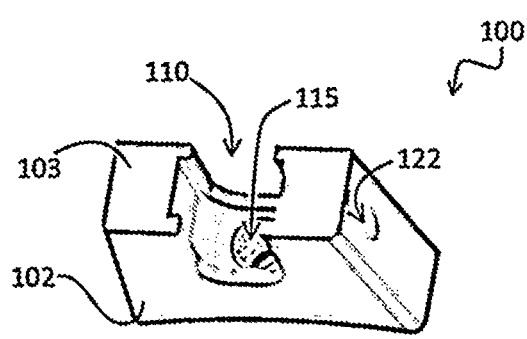
FIG. 1C shows a bottom perspective view of the humeral head cut guide of FIG. 1A.
Figure 1D:
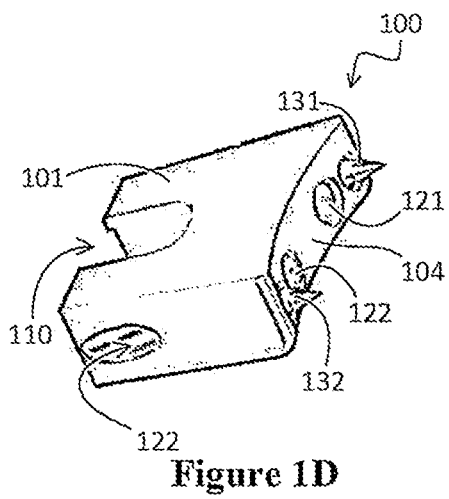
FIG. 1D shows a side, top perspective view of the humeral head cut guide of FIG. 1A.

FIG. 1C provides a clear view of the bottom surface 102 and the back surface 103 of the cut guide 100. The entry point of the right pin channel 122 can be seen on the side of the guide 100, and the threaded opening 115 of the cut guide is visible within the U-shaped receiving portion 110 of the guide. In FIG. 1D, the setting spikes 131, 132 and the exit points of both pin channels 121, 122 are visible on the front surface 104 of the guide 100. Although the entry points of the pin channels 121, 122 are disposed upon the sides of the cut guide 100 in FIGS. 1 and 2, the entry point of the pin channels can be disposed on the back surface 103 of the cutting block 100 in alternative embodiments (see FIG. 8).

Figure 1E:
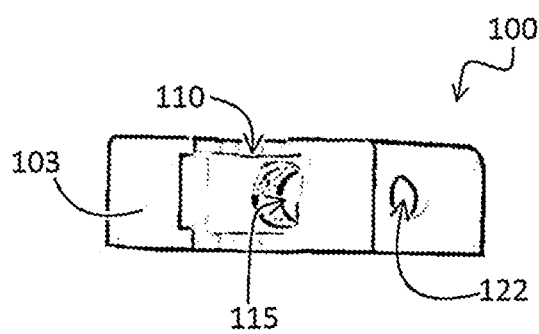
FIG. 1E shows a side perspective view of the humeral head cut guide of FIG. 1A.
Figure 1F:
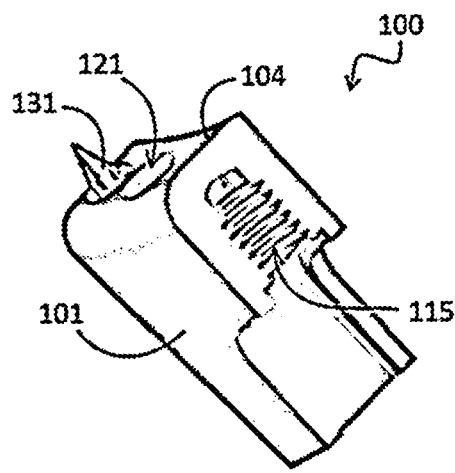
FIG. 1F shows cross-sectional view of the humeral head cut guide of FIG. 1A cut through the vertical axis of the guide.
Figure 2A:
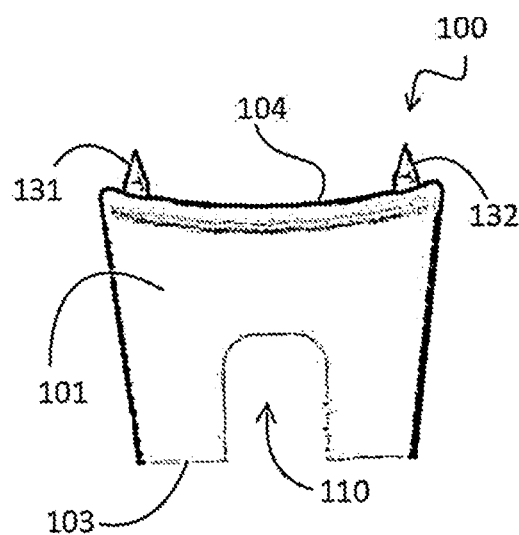
FIG. 2A shows a top view of the humeral head cut guide of FIG. 1.
Figure 2B:
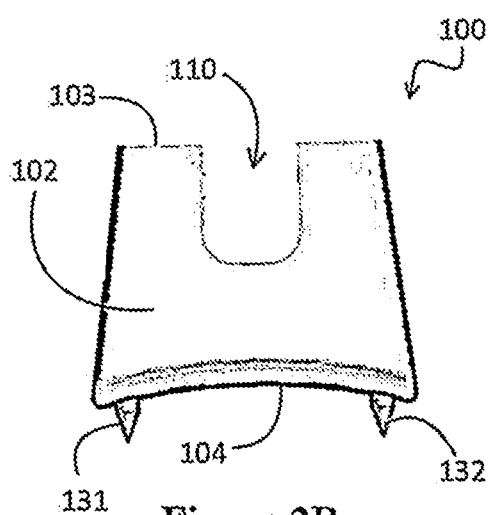
FIG. 2B shows a bottom view of the humeral head cut guide of FIG. 1.
Figure 2C:
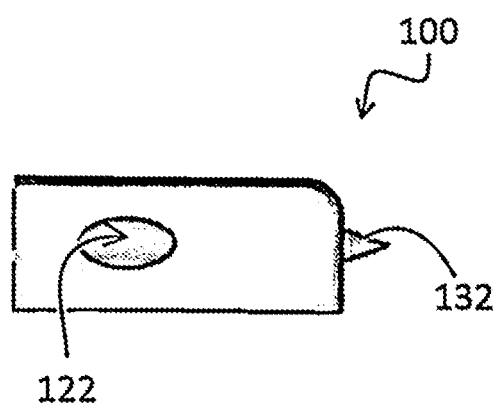
FIG. 2C shows a right side view of the humeral head cut guide of FIG. 1.
Figure 2D:
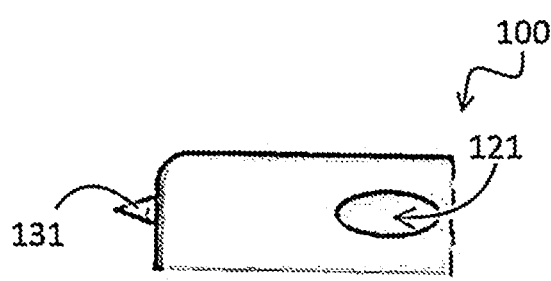
FIG. 2D shows a left side view of the humeral head cut guide of FIG. 1.
Figure 2E:
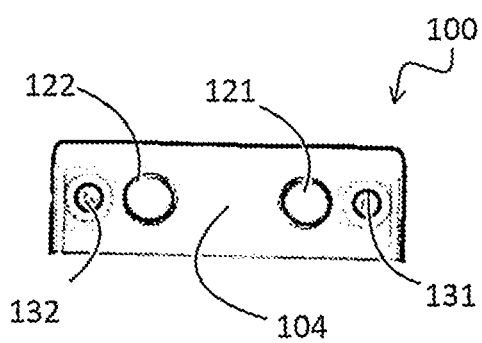
FIG. 2E shows a front view of the humeral head cut guide of FIG. 1.
Figure 2F:
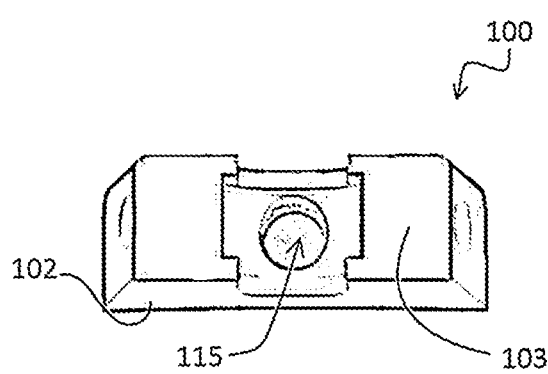
FIG. 2F shows a back view of the humeral head cut guide of FIG. 1.

FIG. 1E provides a clear view of the entire right pin channel 122 extending transversely across the guide 100. The cross-sectional view of FIG. 1F provides an unobstructed view of the threaded opening 115 extending partially into the cutting guide 100.

FIG. 2 provides additional views of the cutting guide under the embodiment of FIG. 1.

The humeral head cut guide 100 can comprise various shapes and sizes that are configured to fit within an opened rotator interval (described in more detail below). In embodiments, the front surface 104 of the cut guide 100 is longer than the back surface 103. The length of the front surface 104 can be between about 110% and 200% the length of the back surface 103. In certain embodiments, the length of the front surface 104 is from about 115% to about 150% the length of the back surface 103. The length of the front surface 104 can be between about 120% to 130% the length of the back surface 103. In one embodiment, the length of the front surface 104 is about 125% the length of the back surface 103. In an alternative embodiment, length of the the front surface 104 is about 120% the length of the back surface. The front surface can be up to about 75 mm in length. The front surface 104 can be between about 10 mm to about 50 mm long. In embodiments, the front surface 104 is between about 15 mm to 40 mm long. The front surface 104 can comprise a length of up to 35 mm. In embodiments, the front surface 104 is between about 20 mm to 30 mm. In embodiments, the length of the front surface 104 is about 20 mm, 21 mm, 22 mm, 23 mm, 24 mm, 25 mm, 26 mm, 27 mm, 28 mm, 29 mm, or 30 mm. In one embodiment, the front surface is about 25 mm long. In an alternative embodiment, the front surface 104 is about 30 mm long.

The back surface 130 of the guide 100 can be up to about 50 mm in length. The back surface 103 can be between about 5 mm to about 40 mm long. In embodiments, the back surface 103 is between about 10 mm to 30 mm long. The back surface 103 can comprise a length of between about 15 mm to 25 mm. In embodiments, the length of the back surface 103 is about 15 mm, 16 mm, 17 mm, 18 mm, 19 mm, 20 mm, 21 mm, 22 mm, 23 mm, 24 mm, or 25 mm. In one embodiment, the back surface 103 is about 20 mm long. In an alternative embodiment, the back surface 103 is about 25 mm long.

The length of at least one side of the guide 100 can be up to about 50 mm. At least one side can be between about 5 mm to about 40 mm long. In embodiments, at least one side is between about 10 mm to 30 mm long. At least one side can comprise a length of between about 15 mm to 25 mm. In embodiments, at least one side is about 15 mm, 16 mm, 17 mm, 18 mm, 19 mm, 20 mm, 21 mm, 22 mm, 23 mm, 24 mm, or 25 mm. In one embodiment, at least one side is about 20 mm long. In an alternative embodiment, at least one side is about 17 mm long.

The height of the cut guide 100 can be continuous across the guide 100. The height of the guide can be up to about 25 mm. The height of the guide 100 can be between about 3 mm to about 2 mm to 15 mm. In embodiments, the height of the guide 100 is between about 5 mm to 10 mm. The guide 100 can be 5 mm, 6, mm, 7 mm, 8 mm, 9 mm, or 10 mm in height. In one embodiment, the guide 100 comprises a height of about 8 mm. In an alternative embodiment, the height of the guide 100 is about 7 mm.

In embodiments, the front surface 104 is configured to fit securely around at least a portion of the humeral head of the subject. In embodiments, the front surface 104 of the guide 100 is curved around an arc that is generally complementary to the shape of the subject's humeral head. In one embodiment, the shape of the front surface 104 is generally complementary to that of the average adult humeral head of a human subject.

Figure 11A:
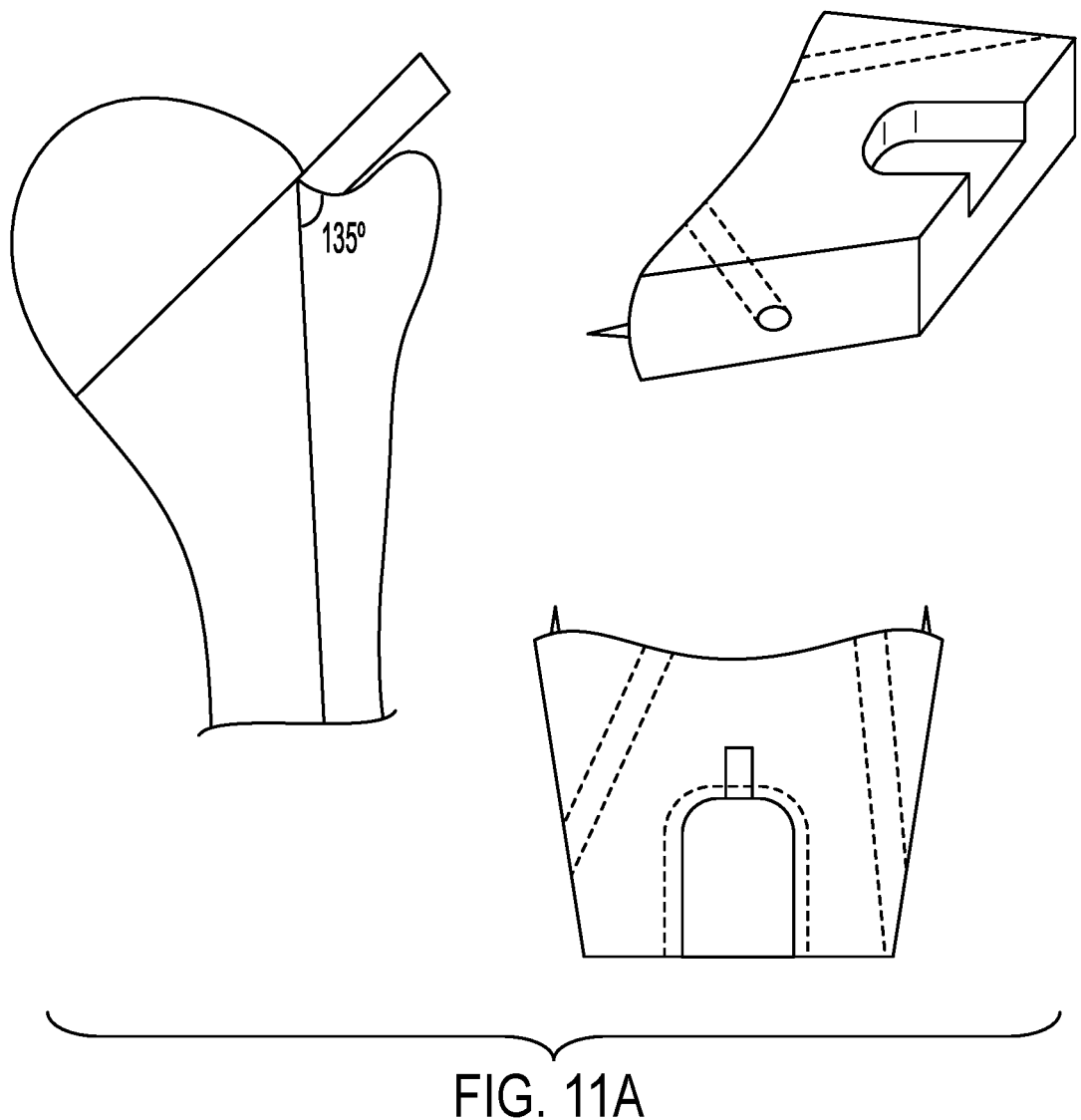
FIG. 11 shows a diagram for a rotator interval humeral head cut guide, under one embodiment.
Figure 11B:
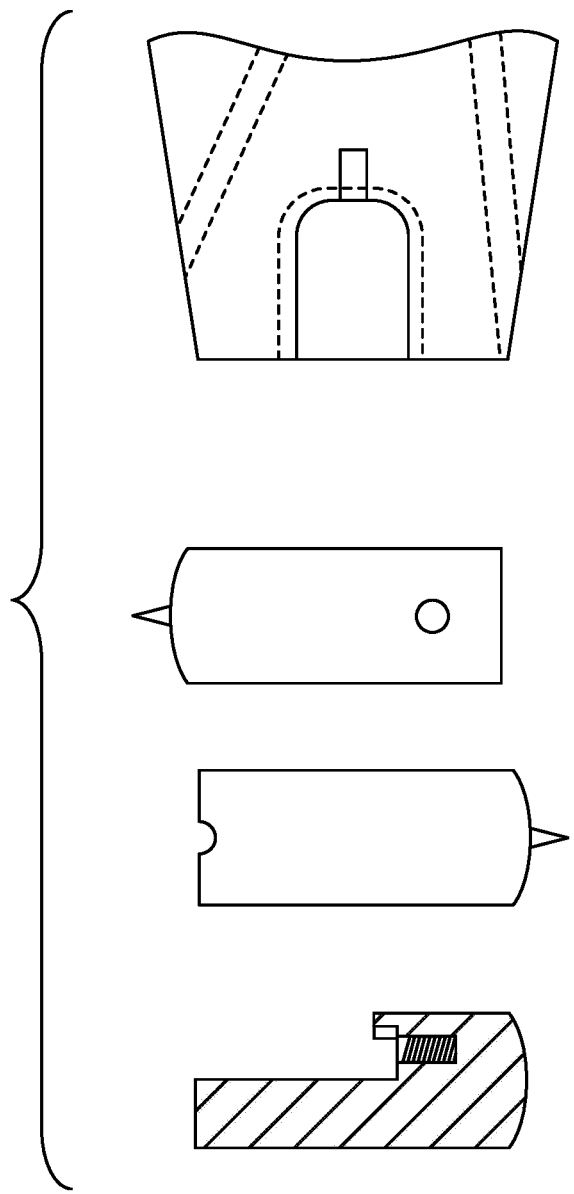
Figure 12:
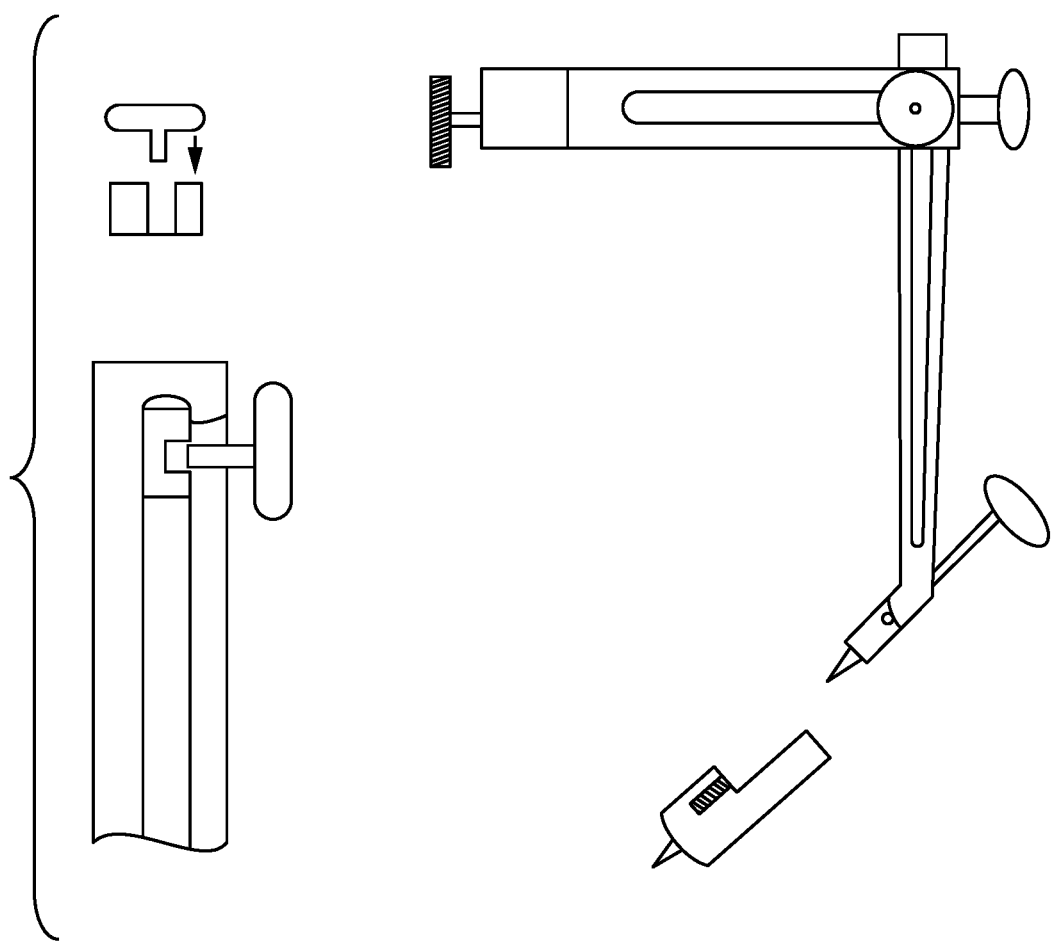
FIG. 12 shows a diagram for an attachment arm assembly, under one embodiment.

In the FIGS. 1, 2, and 11 embodiments, the shape of humeral head cut guide 100 substantially comprises an isosceles trapezoid polyhedron. In embodiments, the humeral head cut guide comprises any trapezoidal polyhedron. The humeral head cut guide can comprise at least two substantially parallel sides. In embodiments, the front surface 104 and the back surface 103 are substantially parallel to one another. Alternative embodiments comprise any polygonal shape. The size, shape, or configuration of the cut guide 100 can vary depending on needs or preferences of the subject or surgeon.

Figure 7:
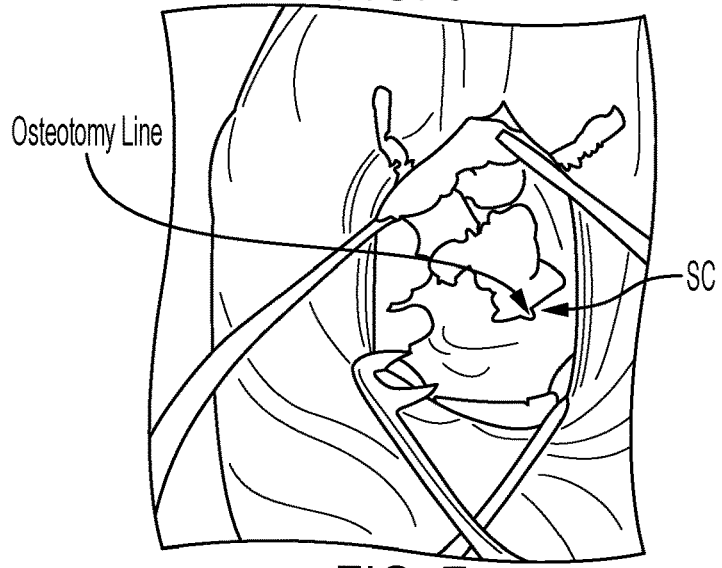
FIG. 7 shows a photographic view of the osteotomy line, created in one embodiment by marking the articular margin to serve as a reference point for cut guide placement and subsequent saw blade entry during humeral head osteotomy.
Figure 8A:
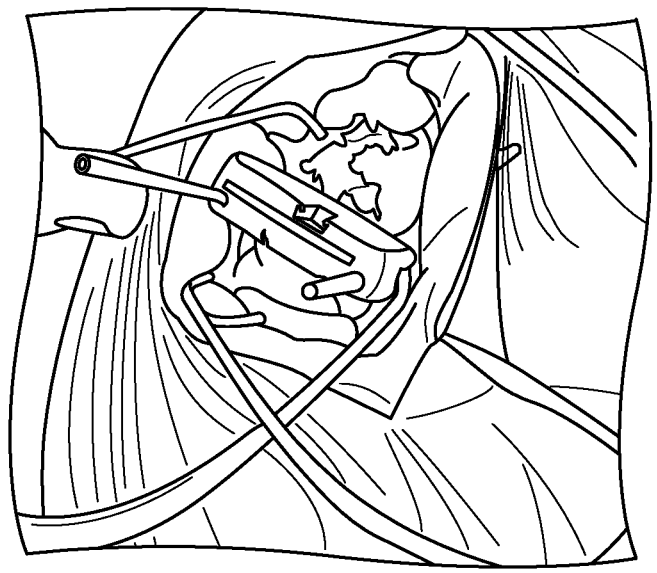
FIG. 8A is a photographic view taken during the rotator interval approach under one embodiment. The humeral head cut guide can be seen inserted between the opened rotator interval.
Figure 8B:
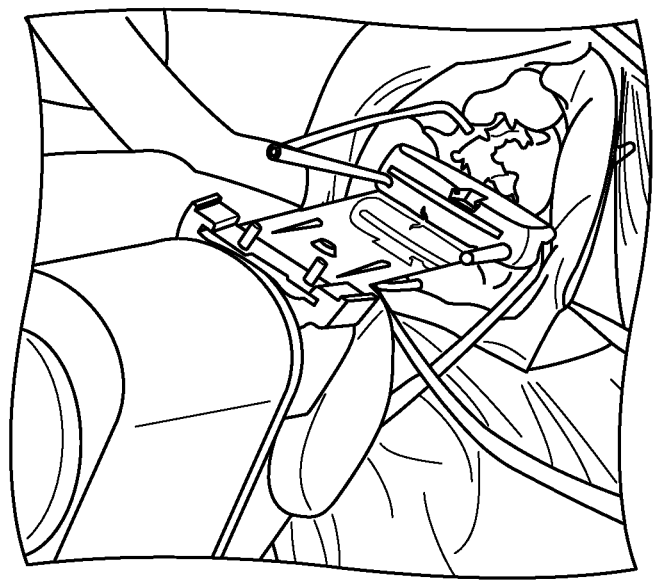
FIG. 8B provides a photographic view taken during the rotator interval approach under one embodiment. A surgical safety saw can be seen using the bottom surface of the humeral head cutting guide during humeral head osteotomy.
Figure 9:
FIG. 9 provides a photographic view taken during the rotator interval approach of another embodiment. Here, a surgical safety saw can be seen using the top surface of the humeral head cutting guide during humeral head osteotomy.

In alternative embodiments, the humeral head cut guide 100 includes a slot that extends transversely through the guide 100 (see the guide shown in FIGS. 7 and 8). In slotted embodiments, the slot is configured to receive the blade of the safety saw for precision cuts of the humeral head.

Additional embodiments can comprise a magnetic guide to further secure the saw in place. In magnetic embodiments, the top or bottom surface of the guide can comprise a plurality of depressions and a steel plate with a plurality of legs that are configured to be magnetically connected to the plurality of depressions. When magnetically connected to the cut guide, the steel plate provides a mechanism for holding the saw in place during humeral head osteotomy.

FIG. 3 shows the attachment arm assembly 200 with the humeral head cut guide 100 reversibly connected thereto. The attachment arm assembly 200 comprises a vertical arm 220 and a horizontal arm 230. The vertical arm 220 is configured to be anchored to the subject during placement of the humeral head cut guide 100. The vertical arm 220 and the horizontal arm 230 are secured to one another via a set screw 210 that extends through a set screw slot of the vertical arm 225 and a set screw slot of the horizontal arm 235. In the FIG. 3 embodiment, the vertical arm further 220 comprises a horizontal arm receiving slot 226 that is configured to receive and hold the horizontal arm 230 therein. When so arranged, the attachment arm assembly 200 can be adjusted to the appropriate height and depth by moving the horizontal arm 230 vertically and horizontally within the horizontal arm slot 226 of the vertical arm 220. After the suitable position is achieved, the set screw 210 can be tightened within the set nut 215 to secure the attachment arm assembly 200 in place. In alternative embodiments, the horizontal arm can contain a receiving slot configured to receive and hold the vertical arm.

The attachment arm assembly 200 of the FIG. 3 embodiment further comprises a cut guide retaining rod 250. The retaining rod 250 includes a portion that is configured to reversibly secure the cut guide 100 to the attachment arm assembly 200 during placement of the cut guide 100 in preparation for humeral head osteotomy. In embodiments, the retaining rod 250 includes a threaded portion that is complementary to the threaded opening of the cut guide (shown at 115 of FIGS. 1B and 1F) and is configured to be threadably inserted therein. In other embodiments, the cut guide 100 is reversibly secured to the retaining arm 250 via alternative means.

Another aspect of the present invention includes a method of shoulder arthroplasty using the humeral head cut guide 100, the attachment arm assembly 200, or both in accordance with any embodiment disclosed within this specification or otherwise apparent from the descriptions herein.

In one embodiment, a subject is placed under general anesthesia and placed in a traditional "beach chair" position with all bony prominences well padded.

A longitudinal incision is made in the skin beginning from about the anteriorlateral acromion. The incision can be an anterosuperior, straight Sabre incision made along Langer's lines. The incision can begin at about 1 cm medial to the anterolateral acromion margin in the anterior-inferior direction. In embodiments, the incision begins at more than 1 cm medial to the anterolateral acromion margin. The skin incision can begin up to about 5 cm medial to the anterolateral acromion margin. The skin incision can begin at about 1 cm, about 2 cm, about 3 cm, about 4 cm, or about 5 cm medial to the anterolateral acromion margin. The length of the incision depends upon the size of the subject. In embodiments, the incision can be between one to ten inches long. The incision can be between two and five inches long. In embodiments, the incision extends for about three to four inches. The incision can be carried medially to the level of the acromioclavicular joint (the "AC joint") and anteroinferiorly to expose the raphe between the middle and anterior deltoid. Gelpi retractors can be employed for subdermal exposure down to deltoid fascia. The length and location of a planned incision under one embodiment can be seen in FIG. 4A.

The deltoid is then split at the raphe between the middle and anterior deltoid. In embodiments, the deltoid split occurs between the anterior and middle heads from the AC joint, along the anterior acromion to 3-4 cm lateral to the acromial edge. In embodiments, the spilt extends for 3-4 cm anterior and inferior to the acromial edge. In embodiments, the deltoid split occurs in the periosteal plane and comprises the shape of a wide V. The Gelpi retractors can then be removed and two self-retaining retractors with blunt tips are placed at right angles to each other to achieve subdeltoid exposure. As shown in the FIG. 4B embodiment, one of the self-retaining retractors can be between the deltoid heads, and the other can retract the skin. In certain embodiments, the self-retaining retractors comprise modified Kolbel self-retaining retractors.

Mobilization of the deltoid is then performed via subdeltoid adhesion release. Subdeltoid adhesions release can be achieved via blunt dissection. In embodiments, the subdeltoid adhesion release is achieved through the use of a Langenbeck elevator, blunt-tipped retractors, the surgeon's finger, or a combination thereof. Mobilization of the deltoid adhesions serves to increase exposure of the underlying tissue. This step is particularly important when the subject has limited pre-operative motion. Bursa can be excised as needed.

The dissection can then proceed through the rotator interval. To achieve the procession, the shoulder can be externally rotated to bring the rotator interval into the field of view. In embodiments, this rotation further places the subscapularis under tension. The rotator interval can be identified by palpating the biceps long head.

Figure 5:
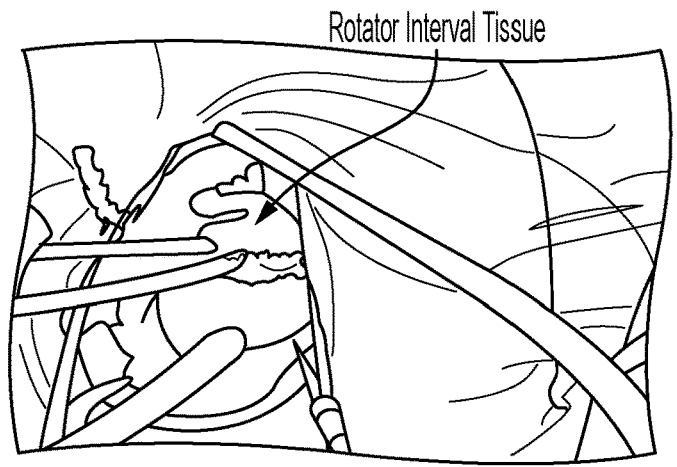
FIG. 5 provides a photographic view of the rotator interval tissue following the incision and splitting of the deltoid.
Figure 6:
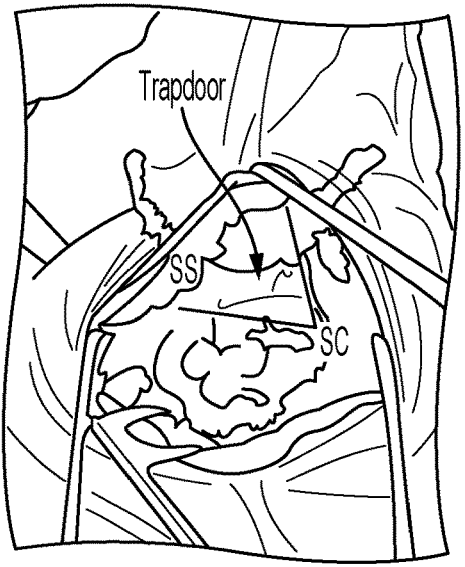
FIG. 6 shows a photographic view of the triangular interval tissue piece or "trap door" attached to the supraspinatus, which is preserved for closure upon completion of the arthroplasty.

The rotator interval is then opened. In embodiments, a flap of interval tissue is incised posterior to the long head of the biceps tendon. Electrocautery can be used to create the flap of rotator interval tissue (see FIG. 5). In embodiments, tissue is cauterized along the lateral greater tuberosity margin from about 5 mm posterior to the biceps tendon to the palpable upper subscapularis margin. The capsule can then be opened in a direct line back to the glenoid. As shown in the FIG. 6 embodiment, when so opened, the tissue creates a "trap door" which is preserved for closing upon completion of the shoulder arthroplasty. Tenodesis of the biceps long head can be performed at the transverse ligament, and the biceps is tenolysed.

In one exemplary embodiment, the "trap door" is created as described within this paragraph. Tissue is electrocauterized from about 5 mm posterior to the long head of the biceps tendon, and the incision exits the shoulder joint and pierces the coracohumeral ligament. The incision is carried down to the articular insertion of the subscapularis. Once the longhead of the biceps is clearly identified, it is released from the supraglenoid tubercle and then tenodesed at the transverse ligament after cauterization of the arcuate artery within the groove. Tenolysation of the biceps distally ensures proper tension of the long head of the biceps. After removal of the biceps tendon from the interval, the interval can be incised back to the glenoid from the upper edge of the subscapularis to create the triangular "trap door" attached to the supraspinatus.

The trap door can then be tucked under the supraspinatus for preservation. In embodiments, the trap door is tucked under the supraspinatus and retracted using blunt-tipped retractors, such as modified Kolbel self-retaining retractors. In embodiments, the the rotator interval can be spread up to 35 mm medially and 35 mm laterally.

As shown in FIG. 7, the junction of cuff attachment with the articular cartilage can then be identified and marked at the articular margin for reference when placing the cut guide 100. In embodiments, a darrach retractor can be used to define the interface between the rotator cuff tendon and the articular cartilage. At this point, the insertion of the subscapularis onto the humerus is readily visible. The hinge point where the supraspinatus attaches at the junction of the humeral articular surface and the greater tuberosity footprint can then be exposed. In certain embodiments, this exposure is accomplished via a second darrach retractor. Electrocautery can then be used to mark the line from the articular side of subscapularis to the articular side of the supraspinatus. As discussed briefly above and shown in the FIG. 7 embodiment, this line will serve as a reference point for cut guide placement and the saw blade entrance during humeral head osteotomy.

The insertion point used to place the attachment arm assembly 200 (also referred to herein as "the intramedullary insertion guide") can then be identified. In one embodiment, this insertion point is posterior to the biceps, nearest the highest point of the humerus. This point can be about 5 mm away from the supraspinatus insertion. In embodiments, the insertion point is about five to ten mm posterior and medial to the bicipital groove. Once located, the intramedullary canal can be opened with a rongeur to prepare for insertion of the attachment arm assembly 200 therein. In embodiments, an anchoring rod of the attachment arm assembly is inserted into the intramedullary insertion point. Before insertion of the guide, the supraspinatus can be retracted out of the cutting plane if present therein.

Figure 4C:
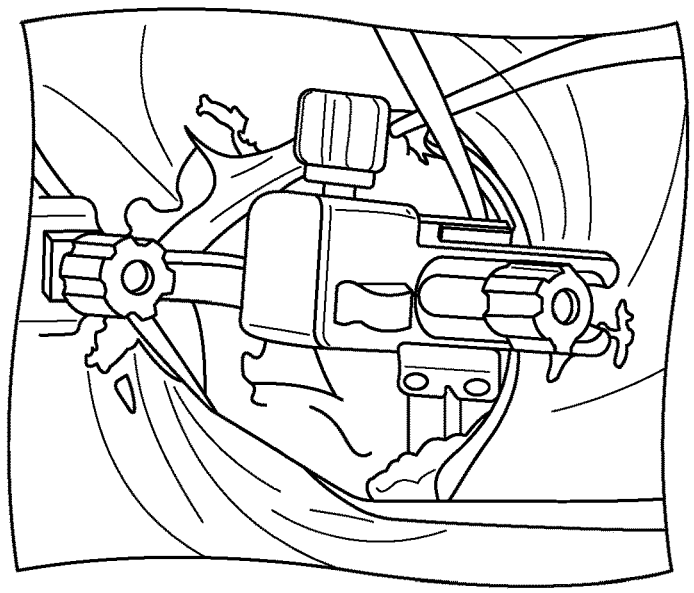
FIG. 4C provides a photographic view of the FIG. 4B incision with the attachment arm assembly in place.
Figure 4B:
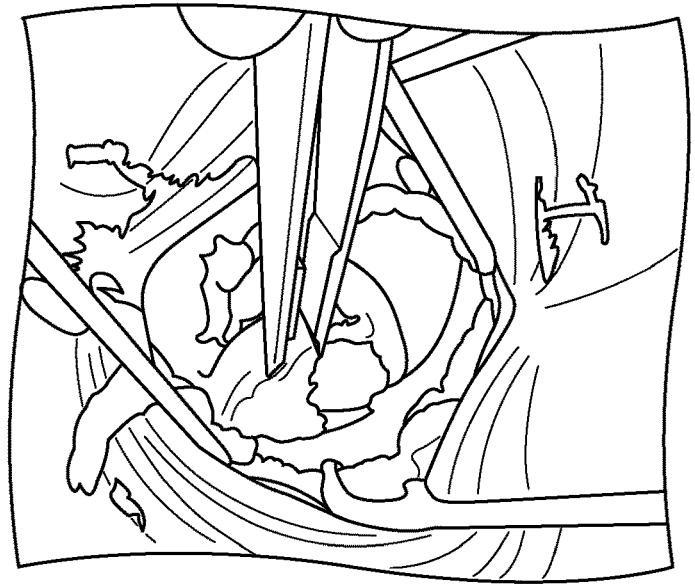
FIG. 4B provides a photographic view of the FIG. 4A subject's shoulder following the incision, splitting of the deltoid heads, and opening of the rotator interval to reveal the humeral head before placement of the humeral head cut guide.
Figure 4A:
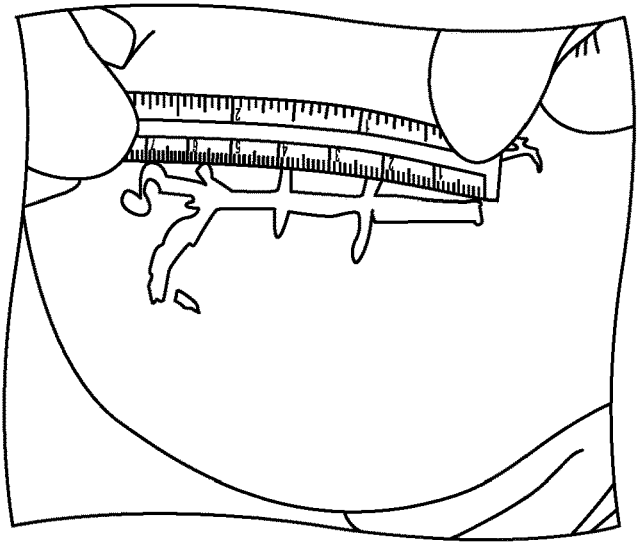
FIG. 4A provides a photographic representation of the planned incision line on the shoulder of a subject in preparation for shoulder arthroplasty via the rotator interval method as disclosed herein.

The anchoring rod or the intramedullary insertion guide of the attachment arm assembly 200 can then be inserted within the intramedullary cannal. In embodiments, insertion of the anchoring rod or guide can be facilitated by extension of the shoulder in adduction with a small darrach under the supraspinatus and infraspinatus. FIG. 4C shows the attachment arm assembly as inserted within the intramedullary canal during placement of the cutting guide, under one embodiment.

The cutting block 100 can then be centered in the opened interval and aligned to begin the cut on the marked articular margin. In embodiments, the bottom surface 102 of the cutting block 100 can be used as a guide for the saw blade (see FIG. 7B). Alternatively, as shown in FIG. 8, the top surface 101 of the cutting block 100 can be used a guide for the saw blade. As shown in FIG. 7A, certain embodiments of the cutting block 100 comprise a slot that can be configured to receive the blade of a surgical saw for guidance during humeral head osteotomy. Retroversion can be between 25-35 degrees, inclusive.

Once properly aligned, the cut guide 100 can be pinned into the appropriate position using the pin channels 121, 122 disposed upon the side or back of the cut guide 100. After pinning the block 100 in place, the attachment arm assembly 200 can be removed from the subject. If necessary, additional adjustment of the cutting block 100 can be made following removal of the attachment arm assembly to optimize the saw cut through the articular margin.

Following placement of the guide, the humeral head can be cut in preparation for humeral head osteotomy. In one embodiment, the humeral head is cut at 132.5 degrees. A safety saw can be utilized for the cutting of the humeral head to avoid injury to the anterior and posterior cuff. In certain embodiments, the middle 80% of the head can be cut followed by removal of the block before completing the cut. After completing the cut, the humeral head can be removed. In embodiments, removal of the cut humeral head can be simplified by making a coronal cut through the head and removing a ¼ to ½ slice of the head. Coronal cuts are particularly useful when the subject has a large shoulder or there are significant abnormalities or deformities of the humeral head.

Figure 10A:
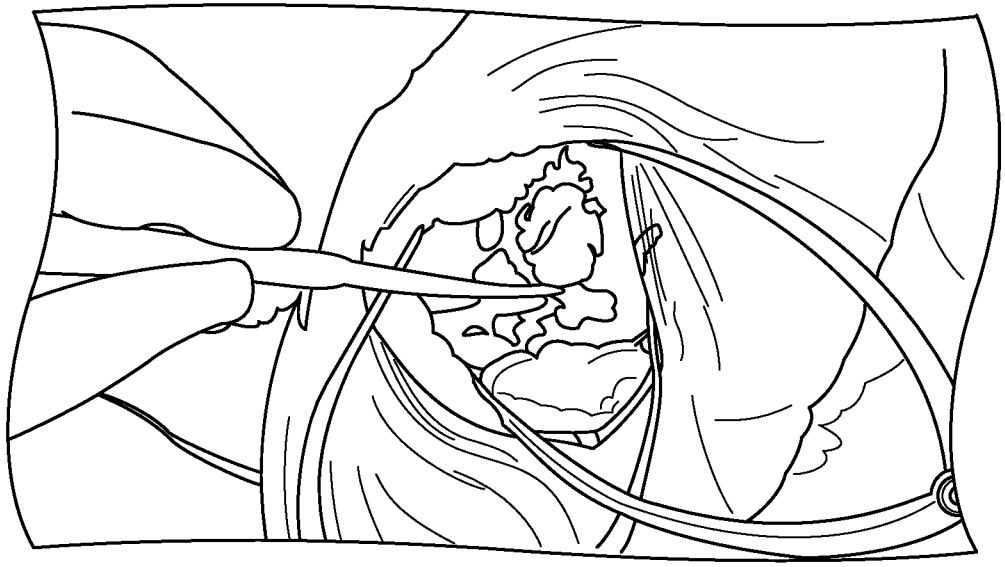
FIG. 10A is a photographic view obtained following removal of the humeral head during the rotator interval approach in one embodiment. The glenoid is clearly visible in the center of the incision.

Following removal of the humeral head, self-retaining retractors can be set deeper and adjusted to maximize exposure of the glenoid (see FIG. 10A). Circumferential resection of the labrum can then be performed. The bicep stump can also be resected. The inferior capsule can then be released from the glenoid. In one embodiment, the inferior capsule is released from approximately the inferior ⅔ of glenoid. In certain embodiments, the inferior capsule is released from 10 O'clock to 2 O'clock in the periosteal plane. In embodiments, the capsule is released to a depth of about 1-2 cm. The capsule can be removed via electrocautery.

The final glenoid component can be placed after sizing, preparation, drilling, and trialing per surgical technique.

Figure 10B:
FIG. 10B is a photographic view obtained following removal of the humeral head during the rotator interval approach of the FIG. 9A embodiment. Here, a glenoid guide is placed over the glenoid in preparation for installation of the glenoid component.

As shown in FIG. 10B, the location of a center hole can be marked upon the glenoid using an appropriate glenoid guide. The center pin can then be placed, and the articular cartilage can be removed with a reamer while preserving the subchondral bone. Next, the center hole can be drilled into the glenoid.

The peripheral pinholes can then be drilled using the guide while adjusting the rotation as needed. In one embodiment, the superior hole is drilled first and secured with a pin. The first inferior hole can then be drilled and subsequently pinned. In certain embodiments, it can be useful to depress the cut humeral surface to improve the accuracy of the fit. The second pin hole can then be drilled and pinned. If required, the guide and pins can be subsequently removed to permit deepening of the peripheral hole.

A glenoid trial can then be inserted and impacted to achieve a good circumferential fit. Cement can then be inserted into the peripheral peg holes followed by insertion of the glenoid component. In embodiments, the surgeon can check to ensure that no soft tissue is trapped between the component and the glenoid.

After determination of the appropriate replacement humeral head size, the humerus can be sound and broach trialed using the version angle guide.

Figure 13:
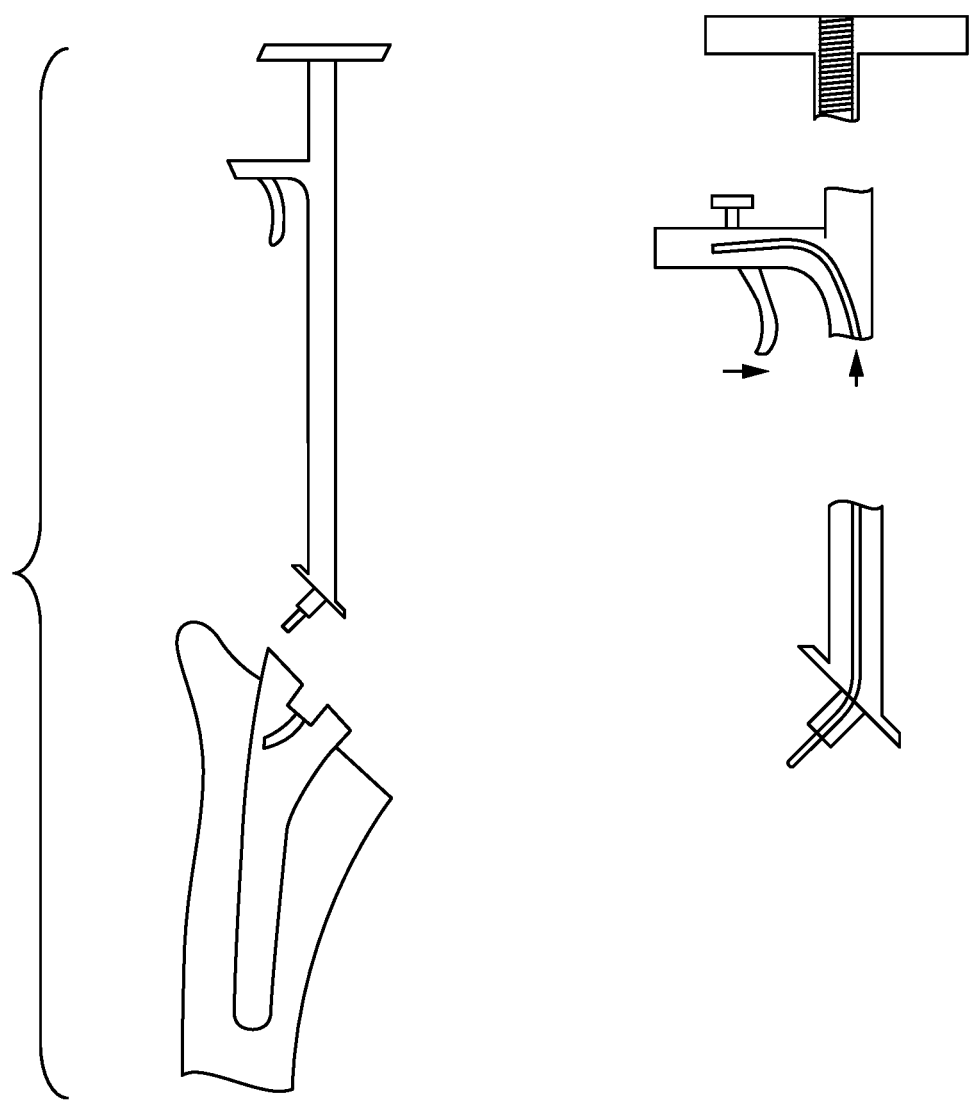
FIG. 13 shows a diagram for a rotator interval humeral broach/STEM insertor/extractor, under one embodiment. The interval approach prevents use of currently available insertors. This insertor/extractor allows the instrument to be brought in from the straight superior direction mandated by the interval approach.

The humeral head stem component can be inserted into the humerus using the rotator interval humeral broach/stem insertor/extractor shown in FIG. 13.

Briefly, the broach/stem insertor/extractor can comprise a strike plate connected to a rod. In one embodiment, the strike plate is configured to be reversibly attached to the rod. The strike plate may comprise a threaded portion for reversible attachment of the striker plate to the rod. In the FIG. 13 embodiment, the rod terminates at an angle that is complementary to that of the cut humeral head. In one embodiment, the angle of rod termination is about 135 degrees. The rod can further comprise a widened area or a small apron configured to facilitate engagement of the insertor/extractor with the broach or stem component. In one embodiment, the rod comprises a channel through which a heavy gauge wire extends. In this embodiment, the wire serves as a pin for insertion of the broach or humeral stem. This wire is particularly useful when the broach or humeral stem comprises a complementary channel configured to receive the pin. The rod may further comprise a means for permitting customization of the wire as needed. In one embodiment, the means for permitting customization of the wire comprises a set screw. In an embodiment, the wire is comprised of nickel titanium or Nitinol. The broach/stem insertor/extractor can further comprise a locking pin trigger that is configured to release the wire upon depression of the trigger. Thus, in operation, the humeral broach or stem can be inserted by applying pressure to the striker plate of the insertor/extractor to set the humeral broach or stem within the humerus. Once an appropriate humeral broach or stem is inserted, the locking trigger of the insertor/extractor can be depressed to release the broach or stem from the insertor/extractor.

Figure 17A:
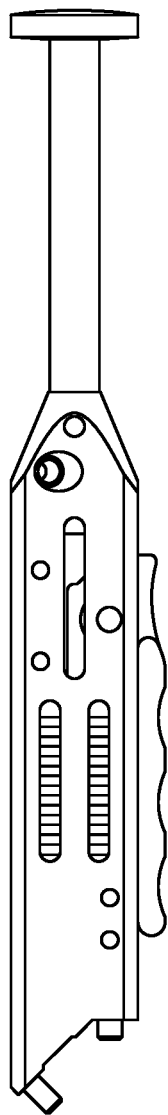
FIG. 17A shows a side view of an insertor/extractor in an alternative embodiment.
Figure 17D:
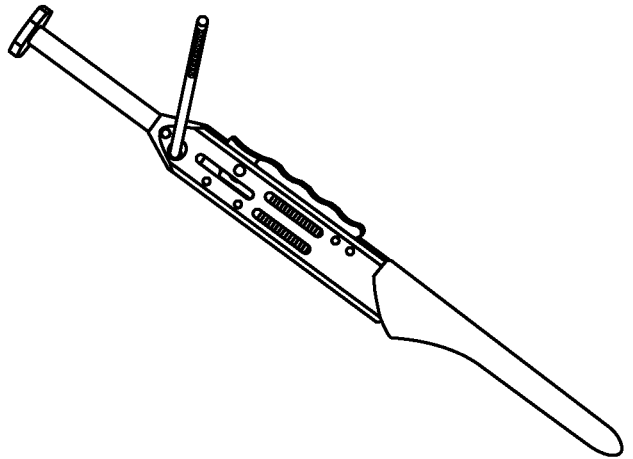
FIG. 17D shows a side view of the insertor/extractor of FIG. 17A. A humeral stem can be seen extending from the stem attachment point of the insertor/extractor.
Figure 17C:
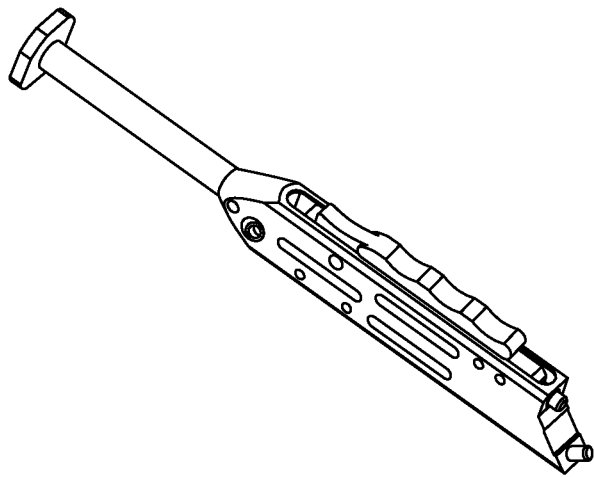
FIG. 17C shows a side perspective view of the insertor/extractor of FIG. 17A.
Figure 17B:
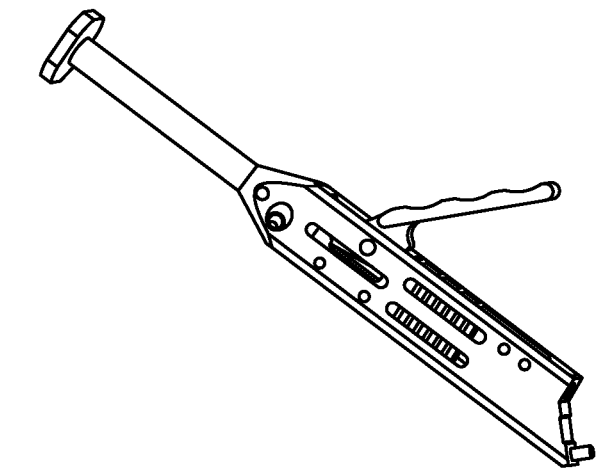
FIG. 17B provides a side view of the insertor/extractor of FIG. 17A with the trigger release mechanism engaged.

An alternative insertor/extractor configured to reversibly engage and hold a broach or stem is provided in FIGS. 17A-17D. As shown in the FIG. 17 embodiment, the alternative insertor/extractor can comprise a trigger that is designed to release the broach or stem from the insertor/extractor, wherein depression of the trigger releases the broach or stem from the insertor/extractor after the humeral broach or stem is inserted into the humerus. FIGS. 17A, 17C, and 17D, show the insertor/extractor with the trigger mechanism in a locked position. In this exemplary embodiment, an engagement mechanism can be seen extending from the termination point of the insertor/extractor. FIG. 17D shows an exemplary insertor/extractor with a stem reversibly attached thereto. As shown in the FIG. 17B embodiment, depression of the trigger mechanism retracts the engagement mechanism and causes a trigger arm to extend from the insertor/extractor. Thus, in this particular embodiment, depression of the trigger releases the broach or stem from the insertor/extractor through retraction of the engagement mechanism. The interior/extractor can be reattached to the broach or stem or attached to a new broach or stem. In embodiments, the insertor/extractor is attached to the broach or stem by inserting the termination point of the insertor/extractor into a receiving portion of the broach or stem followed by depression of the trigger arm to extend the engagement mechanism and return the trigger mechanism to its locked position (see FIGS. 17A, 17C, and 17D). In alternative embodiments, depression of the trigger engages the broach or stem and depression of the trigger arm releases the broach or stem from the insertor/extractor.

Following insertion of the humeral stem component, trialing and insertion of the humeral head prosthesis is completed.

Figure 14A:
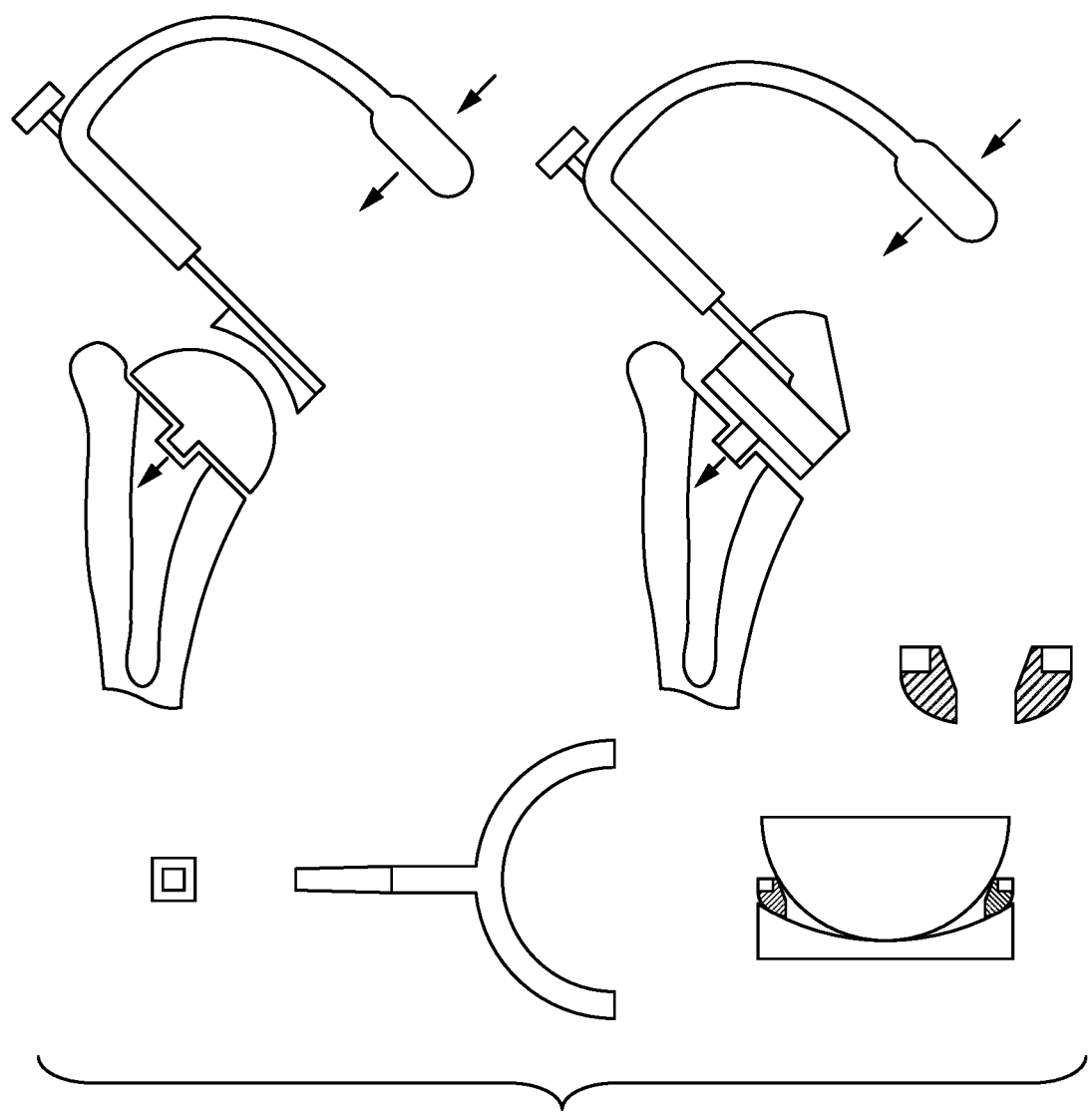
FIG. 14 shows a diagram for a rotator approach bearing assembly modular impactor, under one embodiment. Straight impactors create shear at the Morse taper interface. A low profile curved impactor allows greater compressive force at the Morse taper interface (force arrows →).
Figure 15A:
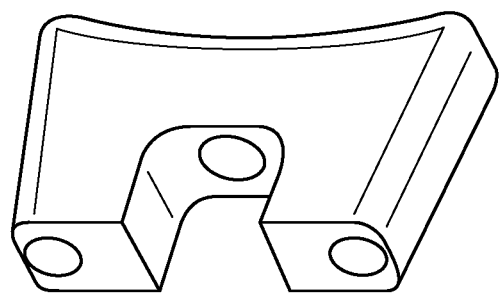
FIG. 15A shows a top perspective view of a humeral head cut guide under an embodiment.
Figure 15B:
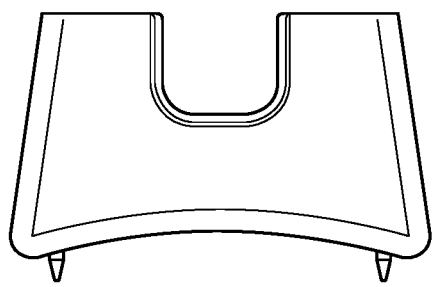
FIG. 15B shows a top view of the humeral head cut guide of FIG. 15A.
Figure 15C:
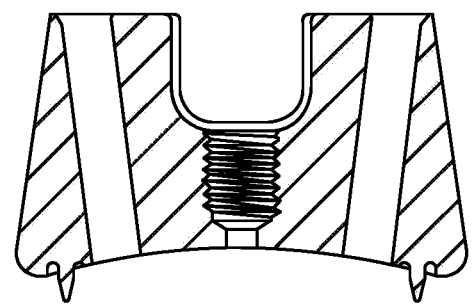
FIG. 15C shows a transverse cross-sectional top view of the humeral head cut guide of FIG. 15A.
Figure 15D:
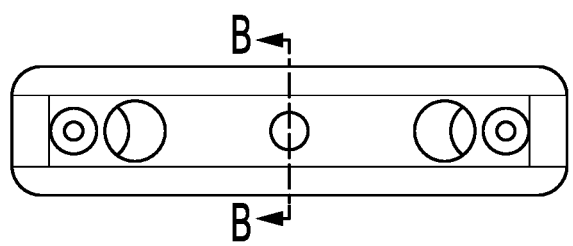
FIG. 15D shows a front view of the humeral head cut guide of FIG. 15A.
Figure 15E:
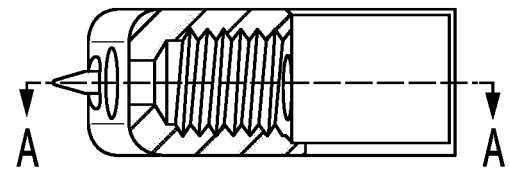
FIG. 15E shows cross-sectional side view of the humeral head cut guide of FIG. 15A cut through the vertical axis of the guide.
Figure 16A:
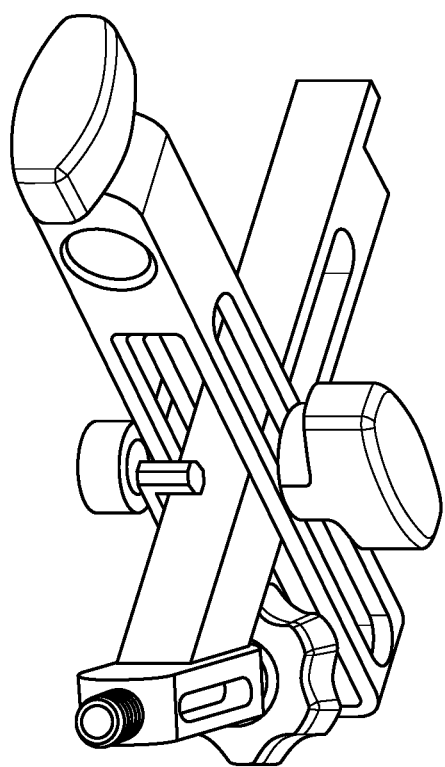
FIG. 16A shows a bottom perspective view of an attachment arm assembly in an alternate embodiment.
Figure 16B:
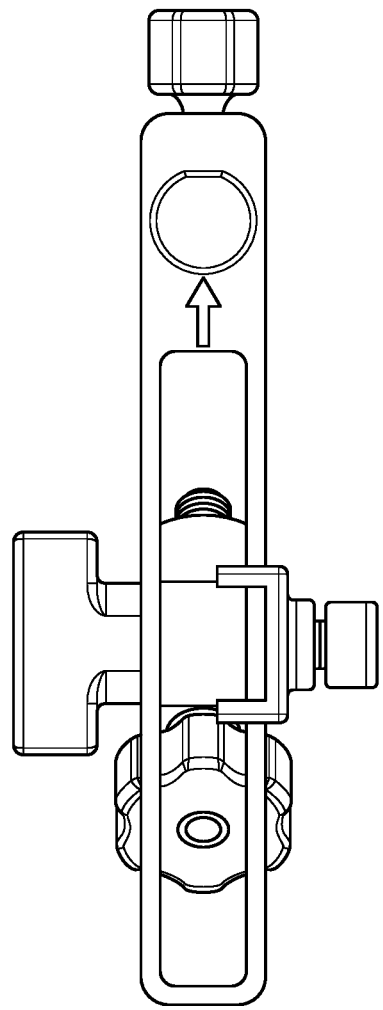
FIG. 16B shows a top view of the attachment arm assembly of FIG. 16A.
Figure 16C:
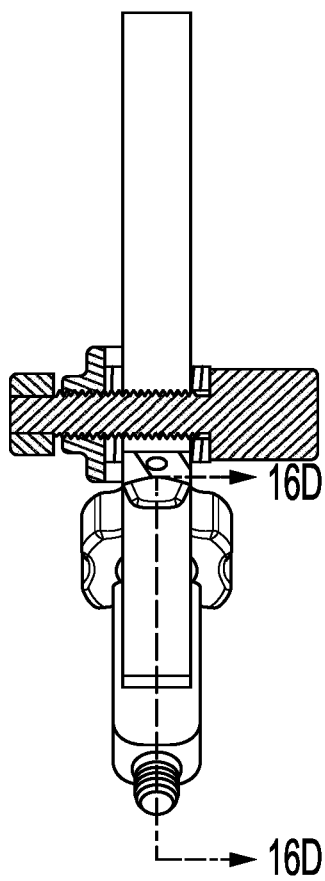
FIG. 16C shows a cross-sectional bottom view of the attachment arm assembly of FIG. 16A. The cross-section is taken through line A of FIG. 16B.
Figure 16D:
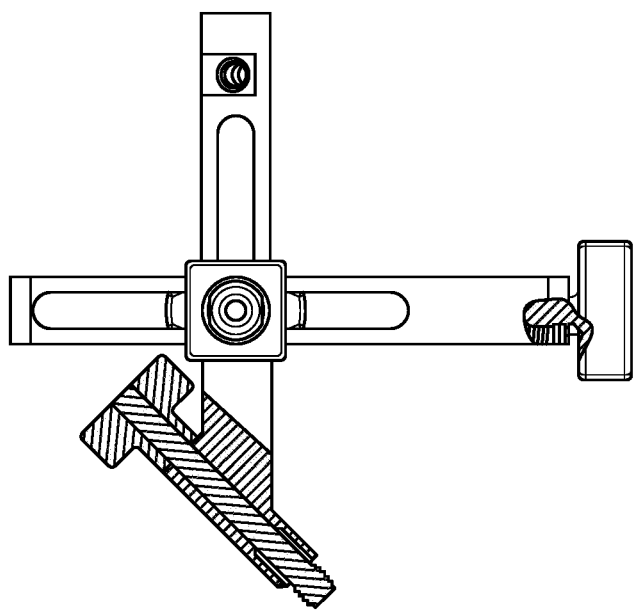
FIG. 16D provides a side cross-sectional view of the attachment arm assembly of FIG. 16A. The cross-section is taken through line B of FIG. 16D.

The humeral head prosthesis can be impacted using the curved impactor shown in FIG. 14. The curved impactor represents an improvement over straight impactors when employing the rotator interval approach of shoulder arthroplasty as described herein because a straight impactor introduces shear at the Morse taper interface, which reduces the compressive force. As shown in FIG. 14, a low profile, curved impactor, as disclosed herein, permits maximal compressive force when impacting the humeral head prosthetic into the humeral stem using the rotator interval approach.

Closure of the surgical site can be performed after insertion of the humeral head prosthesis.

In embodiments, closure comprises retrieval and closing of the trap door tissue. Closure of the trap door can be achieved using absorbable interrupted suture. The deltoid can then be closed medially and laterally. In one embodiment, #2 nonabsorbable inverted transosseous suture is used for medial closure of the deltoid, and #0 absorbable suture is used for lateral closure. Finally, the skin can be closed via the surgeon's preferred method.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

The Rotator Interval Approach for Total Shoulder Arthroplasty

The procedure comprises the following steps:
1. POSITIONING Beachchair, with the patient at the edge of the table so that the arm can be easily brought over the side of the table. Use a hip bolster for security and a low armboard for support of the arm.
2. SKIN INCISION Sabre incision from the anteriorlateral acromion 3-4", in Langer's lines; Gelpi retractors for subdermal exposure down to deltoid fascia.
3. DELTOID SPLIT Between the anterior and middle heads from the acromioclavicular joint, along the anterior acromion to 3 cm lateral to the acromial edge. Remove Gelpi retractors and use modified Kolbel self-retaining retractors placed at right angles to each other; one is between the deltoid heads, the other retracts skin.
4. MOBILIZE DELTOID Release subdeltoid adhesions bluntly, adjusting Kolbel retractors as needed. Excise bursa as needed, rotate the shoulder and identify the rotator interval by palpating the biceps long head.
5. OPEN THE ROTATOR INTERVAL Use cautery along the lateral greater tuberosity margin from 5 mm posterior to the biceps tendon to the palpable upper subscapularis margin; then open the capsule in a direct line back to the glenoid, creating a 'trap door' of capsular tissue which is preserved by placing it under the Kolbel retractor. Tenodesis of the biceps long head is done at the transverse ligament and the biceps is tenolysed.
6. IDENTIFY THE ARTICULAR CARTILAGE MARGIN Use a small darrach retractor to feel the junction of cuff attachment with articular cartilage; mark this margin with cautery
7. IDENTIFY THE ENTRY POINT FOR THE INTRAMEDULLARY GUIDE This point is usually 5-10 mm posterior and medial to the bicipital groove. Insert the guide; this can sometimes be facilitated by extension of the shoulder in adduction with a small darrach under the supraspinatus and infraspinatus.
8. PIN THE GUIDE The cutting block is centered in the opened interval with the slot aligned to begin the cut on the marked articular margin. Retroversion is typically 25-35 degrees. Pin the block, remove the rod and adjust the block as needed to optimize the saw cut through the articular margin.
9. CUT THE HUMERAL HEAD Using a safety saw and protecting the cuff as needed with a darrach. It is often best to cut the middle 80% of the head, remove the block and finish the cut. Removing the cut head is often eased by making a coronal cut through the head and removing a ¼ to ½ slice of the head. Finish any cortical margin cuts as needed, protecting the soft tissues with a darrach.
10. EXPOSE THE GLENOID Readjust the Kolbel retractors to maximize glenoid exposure. Fully excise the labrum and release the inferior capsule from the glenoid from 10 O'clock to 2 O'clock in the periosteal plane 1-2 cm deep. Check the release with a Langenbock elevator and release more as needed.
11. ASSESS ANY REMAINING GOATBEARD OSTEOPHYTE Carefully remove with osteotome and curettes as required.
12. CENTER THE GLENOID PREPARATION Mark the center hole using the appropriate glenoid guide, being sure to visualize all glenoid margins. Place the center pin and remove articular cartilage with the reamer, preserving subchondral bone. Drill the center hole.
13. DRILL PERIPHERAL HOLES Using the guide, adjust rotation as needed. Drill the superior hole first and secure with a pin. Drill the first inferior hole and pin; it may be useful to depress the cut humeral surface with the drill shaft in order to have an accurate fit. Pin the second inferior hole, remove the guide and pins; deepen the peripheral holes as needed.

14. TRIAL THE GLENOID When the glenoid trial is inserted and impacted with good circumferential fit, mix a small amount of cement. Remove the trial, irrigate and dry the glenoid. Use a 10 cc syringe to insert cement into the peripheral peg holes, pressuring with a fingertip. After excess cement is removed, insert the glenoid component and check to insure no soft tissue is trapped between the component and the glenoid.
15. HUMERAL PREPARATION Using upward pressure on the elbow, deliver the cut humeral surface into the operative field, being careful of the glenoid component. Measure the cut humeral surface in several diameters in order to estimate the desired humeral head size. Sound and broach trial the humerus using the version angle guide. I recommend NOT removing the inserter handle. Remove the broach.
16. INSERT THE HUMERAL STEM COMPONENT I leave the component about 1 mm proud. Check for any humeral bone that might prevent seating of the humeral head Morse taper.
17. TRIAL THE SELECTED HEAD Insure there is no impingment of the cuff tendons. Note the head rotation number in the rotator interval and check balancing of the shoulder joint. Remove the head trial.
18. HUMERAL HEAD INSERTION Irrigate and dry the humeral Morse taper socket. Insert and orient the humeral head component using the fork, making sure no soft tissue is trapped. Seat the Morse taper and check. In some embodiments, one may have to adjust or even remove the Kolbel retractor to insert the head easily.
19. FINAL CHECK Check stability and sweep the soft tissues with an elevator to insure there is no entrapment.
20. CLOSURE Retrieve and close the trap door tissue anatomically using absorbable interrupted suture. Close the deltoid medially with #2 nonabsorbable inverted transosseous suture and laterally with #0 absorbable suture. Close the skin by your preferred method (I close subq and subcuticular with absorbable suture). Apply waterproof adhesive; final dressing is a nonadherent strip, single gauze and Tegaderm™.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:
1. A surgical tool comprising:
a humeral head cut guide configured to fit within a rotator interval of a subject in need of shoulder arthroplasty;
the cut guide further comprising:
a top surface, a bottom surface, a front surface, a back surface, and at least two sides, each of the two sides defining a flat surface extending from the back surface to the front surface and from the top surface to the bottom surface;
at least two nonconverging pin holes, each pin hole extending transversely from an entry point located on a side of the cut guide to an exit point on the front surface of the cut guide; and
a receiving portion configured to permit reversible attachment of the cut guide to an attachment arm assembly and detachment of the cut guide from the attachment arm assembly, the receiving portion terminating in a threaded opening that extends partially into the cut guide and is configured to further secure the cut guide to the attachment arm assembly.
2. The surgical tool of claim 1, wherein the cut guide is substantially trapezoidal in shape.
3. The surgical tool of claim 1, wherein the front surface of the cut guide is configured to fit securely on the humeral head of the subject.
4. The surgical tool of claim 3, wherein the front surface of the cut guide is curved around an arc that is configured to be substantially complementary to a shape of the subject's humeral head.
5. The surgical tool of claim 1, wherein each pinhole extends from one side of the cut guide to the front surface of the cut guide.
6. The surgical tool of claim 1, wherein the cut guide further comprises at least two setting spikes that extend outwardly from the front surface of the cut guide and are configured to assist with a placement of the cut guide.
7. The surgical tool of claim 6, wherein the setting spikes extend about 2 to 3 mm from the front surface of the cut guide.
8. The surgical tool of claim 1, the cut guide further comprising a channel configured to receive a blade of a surgical saw, wherein the channel extends from the back surface of the cut guide to the front surface of the cut guide; the channel being further configured to guide the blade during humeral head osteotomy.
9. The surgical tool of claim 1, wherein the front surface of the cut guide is longer than the back surface of the cut guide.
10. The surgical tool of claim 9, wherein a length of the front surface is about 120% a length of the back surface.
11. The surgical tool of claim 9, wherein the front surface is about 30 mm long, and the back surface is about 25 mm long.
12. The surgical tool of claim 1, the cut guide further comprising a height of about 7 mm.
13. The surgical tool of claim 1, wherein at least one of the sides is about 17 mm long.
14. The surgical tool of claim 1, further comprising the attachment arm assembly, the attachment arm assembly comprising:
a vertical arm;
a horizontal arm;
a set screw; and
a cut guide retaining rod.
15. The surgical tool of claim 14, wherein
the cut guide retaining rod is configured to reversibly secure the cut guide to the attachment arm assembly and detachment of the cut guide from the attachment arm assembly.
16. The surgical tool of claim 15, wherein the receiving portion of the cut guide terminates in a threaded opening, and the cut guide retaining rod comprises a threaded portion that is complementary to the threaded opening of the cut guide.
17. A method for total shoulder arthroplasty using a surgical tool, the method comprising opening of a rotator interval and humeral head osteotomy through the rotator interval, the surgical tool comprising:

a humeral head cut guide configured to fit within the rotator interval of a subject in need of shoulder arthroplasty; the cut guide further comprising:
a top surface, a bottom surface, a front surface, a back surface, and at least two sides, each of the two sides defining a flat surface extending from the back surface to the front surface and from the top surface to the bottom surface;
at least two nonconverging pin holes, each pin hole extending transversely from an entry point located on a side of the cut guide to an exit point on the front surface of the cut guide; and
a receiving portion configured to permit reversible attachment of the cut guide to an attachment arm assembly and detachment of the cut guide from the attachment arm assembly, the receiving portion terminating in a threaded opening that extends partially into the cut guide and is configured to further secure the cut guide to the attachment arm assembly.

18. The method of claim 17, wherein opening of the rotator interval comprises creating a trap door of rotator interval tissue and preserving the trap door for closing upon completion of the shoulder arthroplasty.

19. The method of claim 18, wherein creating the trap door of rotator interval tissues comprises:
cauterizing tissue from about 5 mm posterior to a long head of a subject's biceps tendon, wherein the incision exits the subject's shoulder joint and pierces the subject's coracohumeral ligament;
carrying the incision down to the subject's articular insertion of the subject's subscapularis;
identifying the longhead of the biceps;
releasing the long head of the biceps from the subject's supraglenoid tubercle;
tenodesing the long head of the biceps at the subject's transverse ligament;
removing the biceps tendon from the rotator interval tissue;
incising the rotator interval tissue back to the subject's glenoid from the upper edge of the subscapularis to create a triangular "trap door" attached to the subject's supraspinatus.

20. The method of claim 17, further comprising:
identifying a raphe between the subject's middle and anterior deltoid;
splitting the deltoid between the subject's anterior and middle heads of the deltoid; and
rotating the subject's shoulder to bring the rotator interval into the field of view.

21. The method of claim 17, further comprising:
marking the subject's articular margin to be used a reference when placing the cut guide;
inserting an anchoring rod of the attachment arm assembly into the subject's intramedullary canal;
aligning the cut guide with the marked articular margin;
pinning the cut guide in place over the articular margin; and
removing the attachment arm assembly.

22. The method of claim 21, further comprising:
placing a blade of a surgical saw against the cut guide;
cutting the subject's humeral head; and
removing the cut humeral head through the rotator interval.

23. The method of claim 22, further comprising:
resecting the subject's labrum;
releasing at least a portion of the subject's inferior capsule from the subject's glenoid; and
placing an artificial glenoid component onto the glenoid.

24. The method of claim 23, further comprising:
inserting an artificial humeral head stem into the subject's humerus; and
impacting a humeral head prosthesis onto the artificial humeral head stem.

25. The method of claim 24, further comprising:
providing or obtaining an extractor/insertor that is configured to extract and insert the artificial humeral head stem reversibly attached thereto, the extractor/insertor comprising:
a strike plate;
a vertical rod;
an engagement mechanism; and
a trigger; wherein inserting the artificial humeral head stem comprises:
striking the strike plate to impact the humeral head stem within the humerus; and
depressing the trigger to free the humeral head stem component from the extractor/insertor.

26. The method of claim 24, further comprising:
closing the trap door; and
closing the deltoid split.

* * * * *